(12) United States Patent
Pisharodi

(10) Patent No.: US 7,879,095 B2
(45) Date of Patent: Feb. 1, 2011

(54) METHOD OF INSERTING, ROTATING AND RELEASING A SPRING-LOADED ARTIFICIAL DISK

(76) Inventor: Madhavan Pisharodi, 3475 W. Alton Gloor Blvd., Brownsville, TX (US) 78520-9277

( * ) Notice: Subject to any disclaimer, the term of this patent is extended or adjusted under 35 U.S.C. 154(b) by 0 days.

(21) Appl. No.: 10/804,895

(22) Filed: Mar. 19, 2004

(65) Prior Publication Data

US 2005/0065610 A1 Mar. 24, 2005

(51) Int. Cl.
*A61F 2/44* (2006.01)
(52) U.S. Cl. ............... 623/17.11; 623/17.16; 623/17.13
(58) Field of Classification Search ............ 623/17.11, 623/17.12, 17.13, 17.14, 17.15, 17.16
See application file for complete search history.

(56) References Cited

U.S. PATENT DOCUMENTS

| | | | | |
|---|---|---|---|---|
| 4,309,777 A | | 1/1982 | Patil et al. ............... 3/1.91 |
| 4,401,112 A | | 8/1983 | Rezaian ............... 128/92 |
| 4,553,273 A | | 11/1985 | Wu ............... 623/18 |
| 4,657,550 A | * | 4/1987 | Daher ............... 623/17.11 |
| 4,759,769 A | * | 7/1988 | Hedman et al. ............... 623/17.13 |
| 4,863,476 A | | 9/1989 | Shepperd ............... 623/17 |
| 4,932,975 A | | 6/1990 | Main ............... 623/17 |
| 5,059,193 A | | 10/1991 | Kuslich ............... 606/61 |
| 5,123,926 A | | 6/1992 | Pisharodi ............... 623/17 |
| 5,171,278 A | * | 12/1992 | Pisharodi ............... 128/898 |
| 5,197,978 A | * | 3/1993 | Hess ............... 623/1.18 |
| 5,236,460 A | | 8/1993 | Barber ............... 623/17 |
| 5,290,312 A | * | 3/1994 | Kojimoto et al. ............... 623/17.15 |
| 5,390,683 A | * | 2/1995 | Pisharodi ............... 128/898 |
| 5,443,514 A | * | 8/1995 | Steffee ............... 128/898 |
| 5,458,641 A | | 10/1995 | Ramirez-Jimenez ............... 623/17 |
| 5,522,899 A | | 6/1996 | Michelson ............... 623/17 |
| 5,653,762 A | | 8/1997 | Pisharodi ............... 623/17 |
| 5,658,335 A | * | 8/1997 | Allen ............... 623/17.16 |
| 5,658,336 A | * | 8/1997 | Pisharodi ............... 623/17.16 |
| 5,667,522 A | * | 9/1997 | Flomenblit et al. ............... 606/198 |
| 5,669,909 A | * | 9/1997 | Zdeblick et al. ............... 606/61 |
| 5,800,550 A | * | 9/1998 | Sertich ............... 623/17.16 |
| 5,827,328 A | * | 10/1998 | Buttermann ............... 623/17.13 |
| 5,893,890 A | * | 4/1999 | Pisharodi ............... 623/17.16 |
| 5,989,291 A | * | 11/1999 | Ralph et al. ............... 623/17.15 |
| 6,019,793 A | * | 2/2000 | Perren et al. ............... 623/17.16 |

(Continued)

FOREIGN PATENT DOCUMENTS

DE 3729600 3/1989

(Continued)

*Primary Examiner*—Paul Prebilic
(74) *Attorney, Agent, or Firm*—Wisner & Associates

(57) ABSTRACT

A rotating, locking, spring-loaded disk implant for stabilizing adjacent vertebrae. The implant is substantially rectangular in cross-sectional shape with minimal height and maximal width. The implant is inserted into the space between two adjacent vertebrae from which a portion of the intervertebral disk has been removed and, when positioned in the disk space, rotated to bring the sides of the rectangularly-shaped implant defining the width of the implant, with its larger dimension, into engagement with the bodies of the adjacent vertebrae. A portion of the implant is biased away from the implant and into contact with the adjacent vertebrae to provide a cushioning effect between the implant and the vertebra. A lock is then secured to the implant to resist further rotation of the implant in the disk space.

18 Claims, 8 Drawing Sheets

U.S. PATENT DOCUMENTS

| | | | | |
|---|---|---|---|---|
| 6,080,158 | A * | 6/2000 | Lin | 606/61 |
| 6,176,882 | B1 * | 1/2001 | Biedermann et al. | 623/17.15 |
| 6,206,922 | B1 * | 3/2001 | Zdeblick et al. | 623/17.11 |
| 6,264,655 | B1 | 7/2001 | Pisharodi | 606/61 |
| 6,264,695 | B1 * | 7/2001 | Stoy | 623/17.16 |
| 6,309,421 | B1 | 10/2001 | Pisharodi | 623/17.16 |
| 6,419,705 | B1 * | 7/2002 | Erickson | 623/17.16 |
| 6,419,724 | B1 * | 7/2002 | Monteyne | 75/476 |
| 6,428,576 | B1 * | 8/2002 | Haldimann | 623/17.16 |
| 6,454,806 | B1 * | 9/2002 | Cohen et al. | 623/17.15 |
| 6,478,822 | B1 * | 11/2002 | Leroux et al. | 623/17.14 |
| 6,669,731 | B2 * | 12/2003 | Ralph et al. | 623/17.13 |
| 6,746,484 | B1 * | 6/2004 | Liu et al. | 623/17.16 |
| 6,863,689 | B2 * | 3/2005 | Ralph et al. | 623/17.16 |
| 6,887,273 | B2 * | 5/2005 | Ralph et al. | 623/17.13 |
| 6,936,070 | B1 * | 8/2005 | Muhanna | 623/17.12 |
| 7,776,094 | B2 * | 8/2010 | McKinley et al. | 623/17.16 |
| 2003/0069639 | A1 * | 4/2003 | Sander et al. | 623/17.11 |
| 2004/0111161 | A1 * | 6/2004 | Trieu | 623/17.16 |
| 2008/0215153 | A1 * | 9/2008 | Butterman et al. | 623/17.16 |

FOREIGN PATENT DOCUMENTS

| | | |
|---|---|---|
| EP | 0260044 | 3/1988 |
| WO | 9640016 | 12/1996 |
| WO | 0182844 | 11/2001 |

* cited by examiner

METHOD OF INSERTING, ROTATING AND RELEASING A SPRING-LOADED ARTIFICIAL DISK

BACKGROUND OF THE INVENTION

The present invention relates to a spring-loaded intervertebral disk implant for stabilizing two adjacent vertebrae. More specifically, the present invention relates to rectangularly-shaped disk implants which are expanded in the middle portion and are used as an alternative to spinal fusion.

Treatment of a herniated disk in the neck and in the lumbar region continues to be a challenging field of medicine. The classical treatment for a ruptured disk is diskectomy, i.e., removal of the disk from between the vertebrae. In this process, all or a portion of the intervertebral disk is removed, leaving a defect that may bother the patient throughout the rest of their life and compromising the normal interaction between disk and adjacent vertebrae. A procedure that is sometimes used as an alternative is to replace the disk space with a bone graft, usually bone chips cut from the patient's iliac crest, bringing about fusion of the vertebrae above and below the disk, eliminating the empty space between the vertebrae.

Diskectomy with fusion is not ideal because the replaced bone does not have the function of the cartilaginous tissue of the disk, i.e. no cushioning effect, and has complications because of several factors. First, conventional bone plugs used to pack the disk space do not conform to the space of the disk because the disk bulges maximally in the center. The disk space is wider in the middle and narrower at its anterior and posterior ends. For this reason, many commercially available bone plugs have four contact points, i.e. two at each of the front and back of the disk space. Secondly, access to the disk is from the side of the dorsal spine of the adjacent vertebrae, leaving a space that is "off-center" relative to the bodies of the adjacent vertebrae such that the stability of the implant is even more problematical than might be apparent from the limited contact resulting from the shape of the intervertebral space. Another complication is the possibility of infection or other conditions that may require removal of the implant. Also, if the bone pieces do not fuse, they may eventually extrude out of the disk space, pressuring the nerve roots. The most significant disadvantage is that fusion eliminates all motion at the joint between the two vertebrae, as well as the shock-absorbing/cushioning function of the disk.

Various prosthetic disk plugs, or implants, are disclosed in the art, but all are characterized by limitations of not conforming to the shape of the disk space, lack of stability when inserted off-center, inability to be removed, or other disadvantages. For instance, U.S. Pat. No. 4,863,476 (and its European counterpart, EP-A-0260044) describes an elongated body divided longitudinally into two portions having a cam device movable therebetween for increasing the space between the two body portions once inserted into the disk space. However, that device is generally cylindrical in shape such that the only contact points between the device and the vertebral bodies are at the front and back of the disk space, creating increased likelihood of instability and generally rendering that device unsuitable for use after partial diskectomy.

The art also discloses intervertebral disk prostheses such as U.S. Pat. Nos. 3,867,728, 4,309,777, 4,863,477, 4,932,969, Applicant's own U.S. Pat. No. 5,123,926, and French Patent Application No. 8816184 that may have more general contact with the adjacent disks, and spinal joint prostheses as described in U.S. Pat. No. 4,759,769, but which are not intended for use in fusion of the disks. However, the utility of such devices is also limited by a number of disadvantages, in particular, the same lack of cushioning described above in connection with prior art disk plugs and implants. Further, those implants and prostheses that attempt to address this cushioning problem have generally failed because they are not capable of supporting the load imposed upon them by the active post-surgical patient. Further, many prior implants and prostheses require removal of the disk. Removing the disk is not totally undesirable because removing the intervertebral disk does help prevent problems from recurrent disk herniation through the opening into the intervertebral disk space. However, as with all surgical procedures, it is desirable to utilize as much existing structure as possible and to minimize invasiveness. One reason it is desirable to retain as much of the original disk as possible is that if an implant subsequently fails, or if further surgical intervention is indicated for reasons such as infection, the only alternative that is generally available after removal of the intervertebral disk is fusion.

There is, therefore, a need for a device capable of stabilizing the vertebrae adjacent an intervertebral disk that overcomes the various disadvantages and limitations of spinal fusion procedures and the disk plugs and implants that are used in such procedures, and it is an object of the present invention to provide apparatus and methods for meeting that need.

There is also a need for a device that overcomes the disadvantages and limitations of prior intervertebral disk prostheses and so it is also an object of the present invention to provide apparatus and methods for meeting that need.

There is also a need for a device that can be implanted into the disk space in a procedure that decreases the likelihood of recurrent disk herniation and it is also an object of the present invention to provide apparatus and methods for meeting that need.

There is also a need for a device that combines the function of the disk by retaining as much of the undamaged disk as possible, and by functioning in a similar manner to provide the cushioning effect of the disk, and it is an object of the present invention to provide apparatus and methods for meeting that need.

There is also a need for a device that not only functions to provide the cushioning effect of the intervertebral disk but that also provides the opportunity for the repair of the remaining portion of the disk, and it is an object of the present invention to provide apparatus and methods for meeting that need.

Another need that is apparent from the limitations and disadvantages of prior procedures, disk plugs, and prostheses is the need for a device that maintains the function of the intervertebral disk when implanted between adjacent vertebrae and that is capable of being implanted in a surgical procedure that is minimally invasive and that does not require removal of the entire intervertebral disk, and it is therefore also an object of the present invention to provide apparatus and methods for meeting that need.

Another need that is apparent from the limitations and disadvantages of prior procedures, disk plugs, and prostheses is the need for a device that works with the structure of the intervertebral disk space to maintain as much of the normal function of the disk as possible, and it is also an object of the present invention to provide apparatus and methods that combine the properties of cushioning that can be obtained by utilizing the remaining portion of the disk, stability by utilizing a metal implant, shock absorption by biasing a portion of an insert into engagement with the adjacent vertebrae, a hydrogel that functions to fill gaps in the disk space and to help reconstruct and/or prevent recurrent herniation of the remaining portion of the disk, and if necessary, a medical grade adhesive that helps to hold the remaining portion of the disk together and/or bond the hydrogel to the disk material and/or seal off the opening into the disk space, thereby meeting that need.

Another need that is apparent is the need for a device that is capable of supporting the load imposed upon it when implanted in the disk space while also providing the cushioning function of the natural intervertebral disk and it is also an object of the present invention to provide apparatus and methods for meeting that need.

SUMMARY OF THE INVENTION

These needs are met in the present invention by providing a vertebral disk stabilizer comprising an elongate implant with a lock having a surface formed thereon for bearing against either or both of the adjacent vertebrae detachably mounted to one end of the implant to prevent rotation of the lock relative to the implant. When mounted to the implant to resist rotation of the implant, the bearing surface of the lock is oriented at an angle of approximately 90° to the height of the implant. The implant is provided with an insert that is biased into contact with one or both of the adjacent vertebrae to provide a cushioning effect between vertebrae.

In another aspect, the present invention provides a method of cushioning between an implant in the intervertebral disk space and the vertebrae adjacent the disk space comprising the steps of inserting an elongate implant into the intervertebral disk space with the sides of the implant contacting the adjacent vertebrae, biasing an insert portion of the implant away from the implant and into contact with the adjacent vertebrae, and restraining the implant against further rotation.

DETAILED DESCRIPTION OF THE PREFERRED EMBODIMENTS

Figure 1:
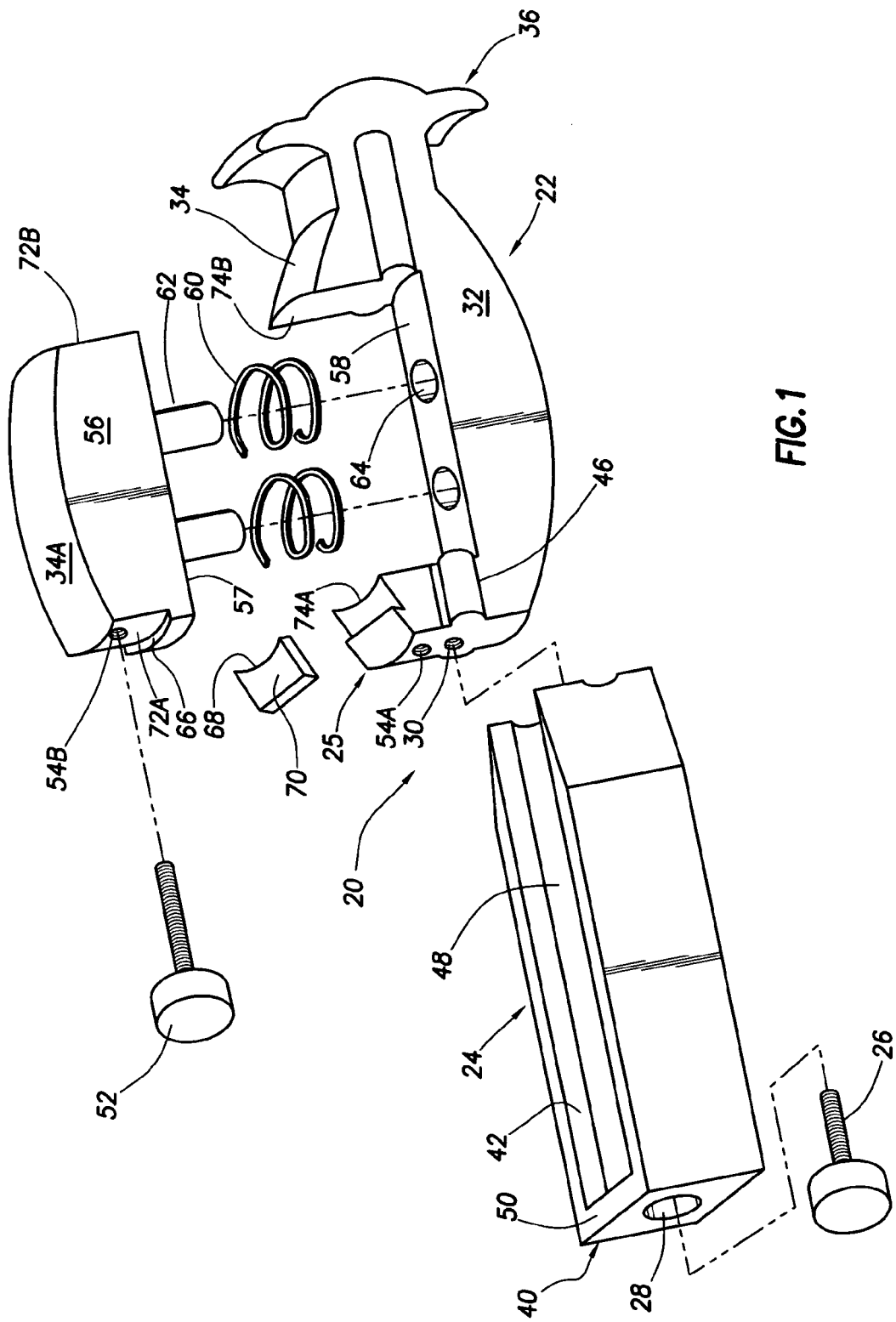
FIG. 1 is an exploded, perspective view of a first embodiment of a vertebral disk stabilizer constructed in accordance with the teachings of the present invention.

Referring now to the figures, a first embodiment of a disk stabilizer constructed in accordance with the teachings of the present invention is indicated generally at reference numeral 20 in FIG. 1. Stabilizer 20 is intended to be implanted between the bodies of two adjacent vertebrae in the disk space from which a portion of the intervertebral disk has been removed, i.e. by simple diskectomy and small laminotomy.

The vertebral disk stabilizer 20 is comprised of an elongate implant 22, lock 24, and means for detachably mounting the lock 24 to one end 25 of the implant 22. In the presently preferred embodiment shown, the mounting means takes the form of a bolt 26 passing through a bore 28 in lock 24, the threads of bolt 26 engaging complementary threads in the walls of the bore 30 in the end 25 of implant 22. A lock nut (not shown) may optionally be provided for resisting the loosening of the bolt 26 once lock 24 is mounted to implant 22 in the manner described below.

In more detail, implant 22 is comprised of first and second sides 32 and third and fourth sides 34 providing a substantially rectangularly shaped cross-section. The height of the rectangularly shaped cross-section is defined by first and second sides 32 and the width is defined by the third and fourth sides 34 and, as is apparent by comparison of the height and width, the width of implant 22 is less than the height. As will be explained below, height is minimized to facilitate insertion of the second end 36 into, and positioning of implant 22 in, the disk space from which a portion of the intervertebral disk has been removed and width is maximized so that, when implant 22 is rotated by approximately 90°, implant 22 provides the desired distraction of the adjacent vertebrae. Third and fourth sides 34 are arched from one end of implant 22 to the other to provide the portion of implant 22 intermediate the ends 25 and 36 with a height that is larger than the height at the ends 25 and 36. Because the sides 32 of implant 22 are substantially flat and the sides 34 are arched from one end 25 to the other end 36, implant 22 is described as being a bi-planar, bi-convex implant. The bi-convex sides 34 of implant 22 are optionally provided with a plurality of teeth (not shown) for biting into the adjacent vertebrae to help resist anterior-posterior movement of implant 22 in the disk space as explained in more detail below. The end 36 of implant 22 is provided with a flare, or "whale tail," 38 for this same reason, it being critical to resist such anterior-posterior movement so as to reduce the likelihood of injury to the nerves of the spinal cord both during insertion of implant 22 into the disk space and after implantation.

Figure 6:
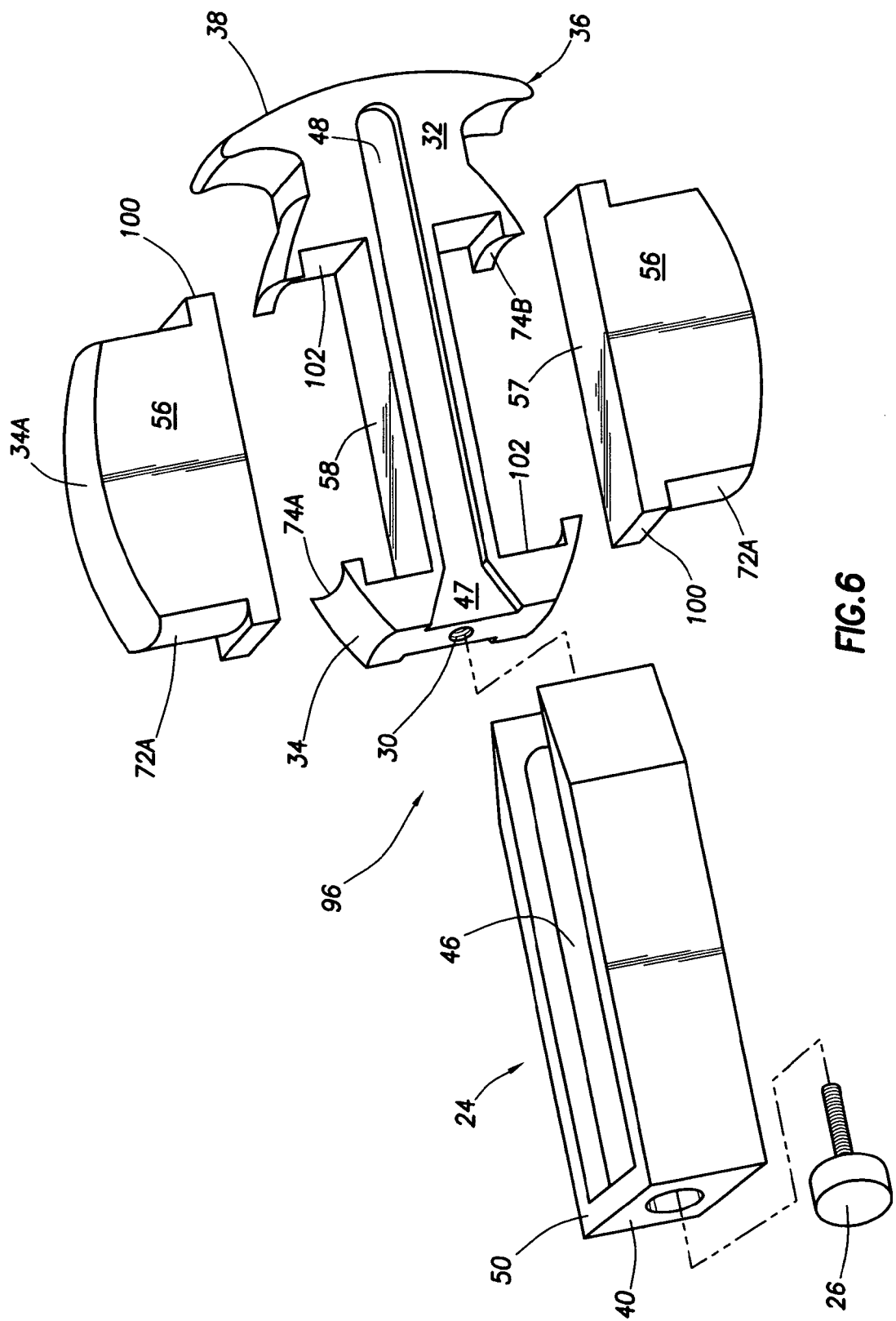
FIG. 6 is an exploded, perspective view of a sixth embodiment of a vertebral disk stabilizer constructed in accordance with the teachings of the present invention.
Figure 7:
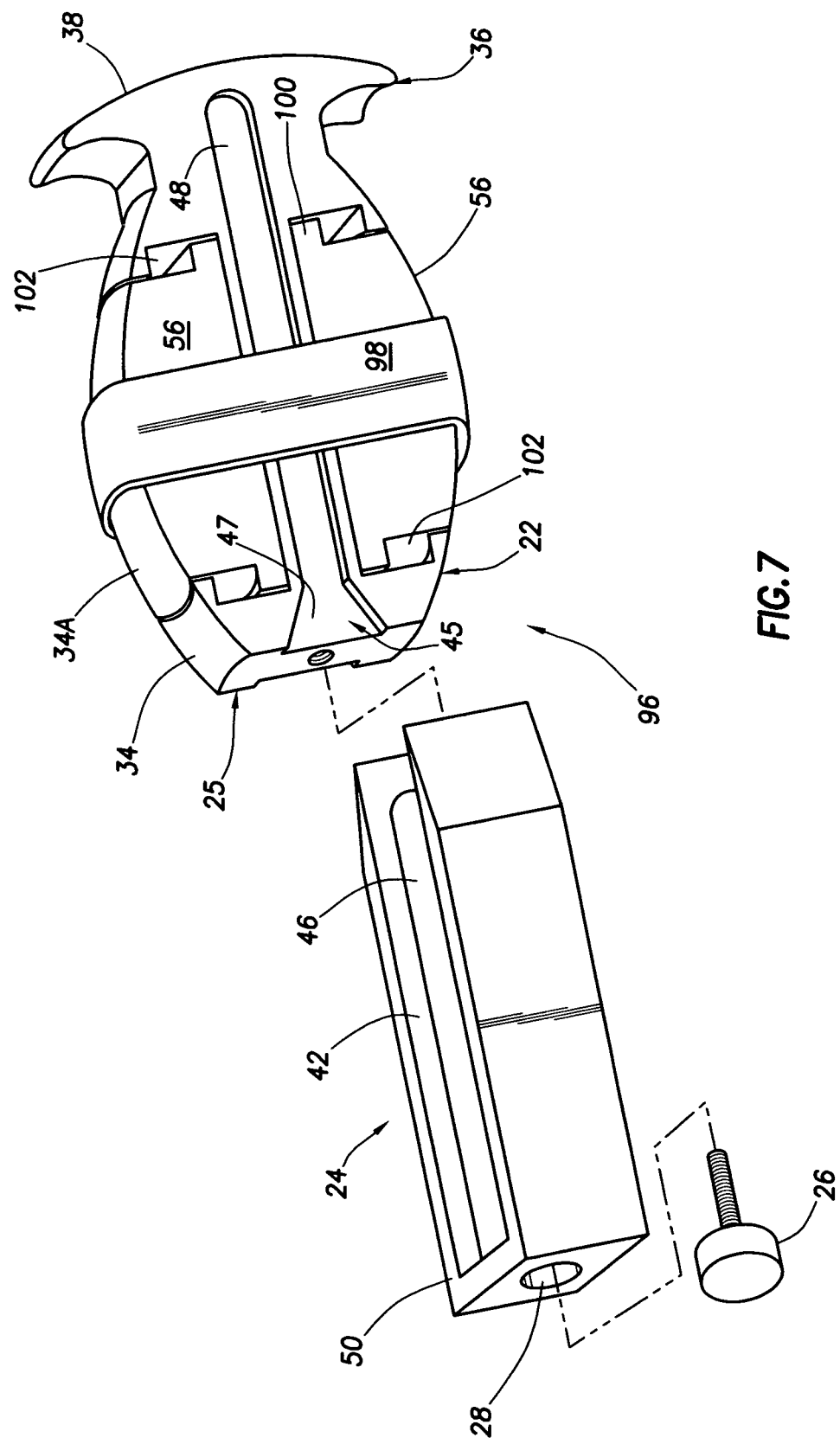
FIG. 7 is a perspective view of the stabilizer of FIG. 6 showing a band for minimizing the height to facilitate insertion into the intervertebral disk space.

In the embodiment shown, lock 24 is substantially square when viewed from the end 40 along the axis of the bore 28 therethrough and "U"-shaped when viewed from the side. The inside surfaces 42 of the arms 44 of the "U"-shaped lock 24 are flat for contacting the first and second sides 32 of implant 22 to prevent rotation of lock 24 relative to implant 22 when lock 24 is mounted to implant 22 and secured thereto by bolt 26. The sides 32 of implant 22 are provided with a key 46 that is received in a complementary-shaped keyway 48 formed in the surface 42 of the arms 44 of lock 24 to facilitate assembly of lock 24 to implant 22; those skilled in the art who have the benefit of this disclosure will recognize that (as shown in FIGS. 6 and 7) the key 46 may be located on the lock 24 and keyway 48 may be located on implant 22 without any difference in the manner in which those component parts function. Although not shown in FIGS. 1-6, in the same manner as described below in connection with FIGS. 6 and 7, those skilled in the art will recognize that the mouth of the keyway 48 at the ends of the arms 44 of lock 24 may be wider than the width of the key 46 to facilatate insertion of keys 46 into keyways 48.

The sides of the square end 40 of lock 24 provide surfaces 50 for bearing against the bodies of the adjacent vertebrae as also explained in more detail below. It will be recognized by those skilled in the art who have the benefit of this disclosure that the bearing surfaces 50 need not be flat and that the end 40 of lock 24 need not be square. Other shapes and configurations may be utilized as needed to insure that movement of lock 24, and the implant 22 once lock 24 is mounted to implant 22, is limited by engagement of the bodies of the adjacent vertebrae by the vertebral bearing surfaces 50. The purpose of the bi-planar, middle expanded, bi-convex implant 22 is to enable insertion of the implant 22 into the disk space and turning by approximately 90° to increase the disk height and stabilize the disk space. The purpose of lock 24 is to lock implant 22 against instability when in the vertical position so as to maintain the disk height thereafter.

An applicator (not shown) of the type described in U.S. Pat. No. 5,658,336, which patent is hereby incorporated into this specification in its entirety by this specific reference thereto, is mounted to the end 25 of implant 22 by screwing the threaded end of the applicator into the threaded bore 30 in implant 22. When the applicator is screwed all the way into bore 30, so as to prevent relative movement therebetween, implant 22 is inserted into the disk space with the wide sides 32 (so that the height of implant 22 is of minimal dimension) proximate the bodies of the adjacent vertebrae and rotated in the disk space by approximately 90° using the applicator so that the minimally-dimensioned sides 34 are proximate the bodies of the adjacent vertebrae so as to maximize the height of implant 22 in the disk space. The procedure for placement of the implant 22 is set out in more detail below. The applicator is then detached from implant 22 by rotating in the opposite direction while rotation of implant 22 is restrained.

After implant 22 has been rotated so as to maximize height in the intervertebral disk space and the applicator is detached from the implant, and before lock 24 is mounted to implant 22 to prevent rotation of implant 22 in the disk space, bolt 52, which extends into the portion of the threaded bore 54A in implant 22 in the end 25 of implant 22 and the portion 54B in the insert portion 56 of implant 22, is backed out of implant 22. Backing bolt 52 out of threaded bore 54B releases insert 56, which is biased away from the landing 58 in the implant 22 by springs 60, from a first, compressed position to a second position in which the insert 56 floats on springs 60 so that the portion 34A of the side 34 of implant 22 comprising insert 56 contacts the body of a vertebra adjacent the disk space. As set out in more detail below, biasing insert 56 toward the adjacent vertebrae (away from the landing 58 of implant 22) in this fashion provides the cushioning function that is lacking from prior known intervertebral implants. The pistons 62 on the underside 57 (the side adjacent landing 58) of insert 56 are received in complimentary-shaped and sized recesses, or blind bores, 64 to maintain alignment of the insert 56 with implant 22 as insert 56 moves relative to implant 22, and a stop 66 formed on one end of insert 56 is engaged by the lip 68 formed by the cap 70 that is secured to implant 22 by cap screw 71 to limit movement of insert 56 away from landing 58. Of course the springs 60 bear against the landing 58 of implant 22 and the underside 57 of insert 56 to bias insert 56 away from landing 58. The adjacent surfaces 72A, 72B and 74A, 74B of insert 56 and implant 22, respectively, are shaped in complementary curves so as to assist in maintaining alignment between insert 56 and implant 22 as insert 56 moves relative to implant 22. Those skilled in the art who have the benefit of this disclosure will recognize that the adjacent surfaces 72A, 72B and 74A, 74B may be provided with a key and keyway or other structure that functions to maintain alignment between insert 54 and implant 22 as insert 54 moves relative to implant 22 in the disk space and that the present invention contemplates any and all such structure that functions in this manner to accomplish the result of maintaining alignment.

Figure 2:
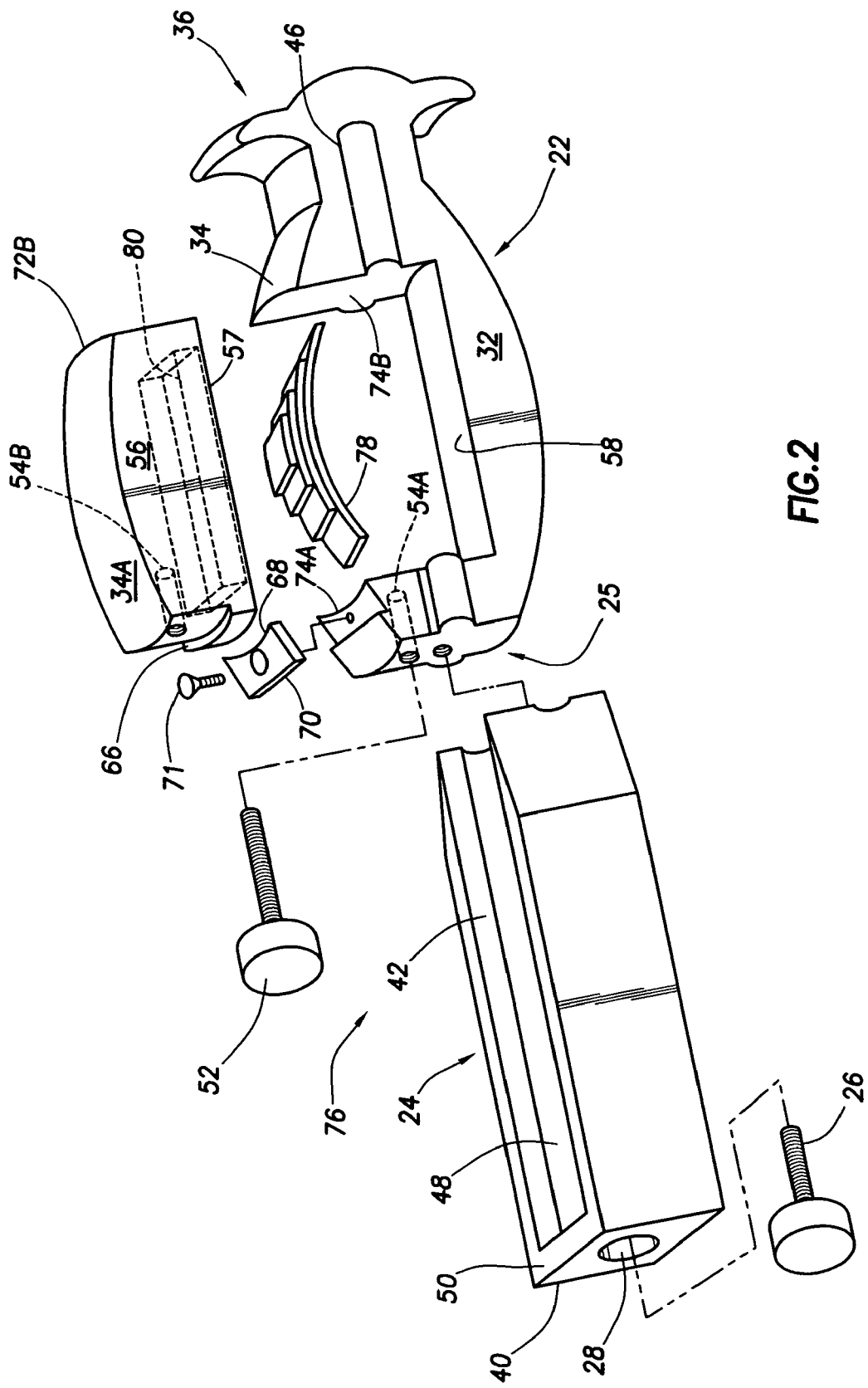
FIG. 2 is an exploded, perspective view of a second embodiment of a vertebral disk stabilizer constructed in accordance with the teachings of the present invention.

Referring now to FIG. 2, a second embodiment of a stabilizer constructed in accordance with the teachings of the present invention is indicated generally at reference numeral 76. Stabilizer 76 includes most of the same component parts as shown in the stabilizer 20 shown in FIG. 1 and the reference numerals utilized in FIG. 2 are therefore the same as are utilized in describing the component parts of stabilizer 20 shown in FIG. 1 (and for the same reason, the same numbering scheme is also utilized in describing the embodiments shown in FIGS. 3-7). Rather than being provided with a pair of coil springs such as are shown in FIG. 1, the stabilizer 76 shown in FIG. 2 is provided with leaf spring 78 that is received within the cavity 80 formed on the underside 57 of insert 56. In spite of this structural difference in the means for biasing insert 56 away from the landing 58 of implant 22, stabilizer 76 functions in the same manner as stabilizer 20.

Figure 3:
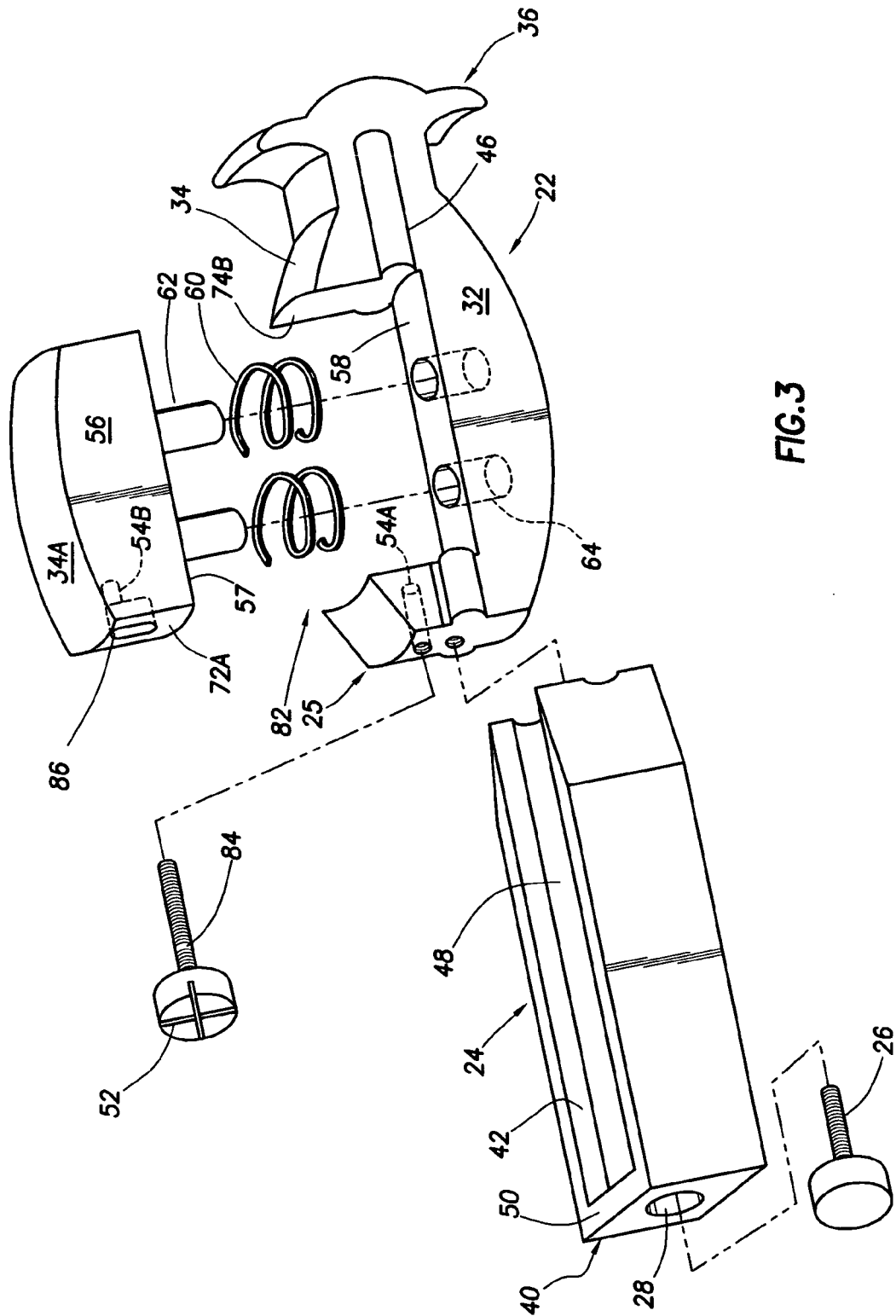
FIG. 3 is an exploded, perspective view of a third embodiment of a vertebral disk stabilizer constructed in accordance with the teachings of the present invention.
Figure 4:
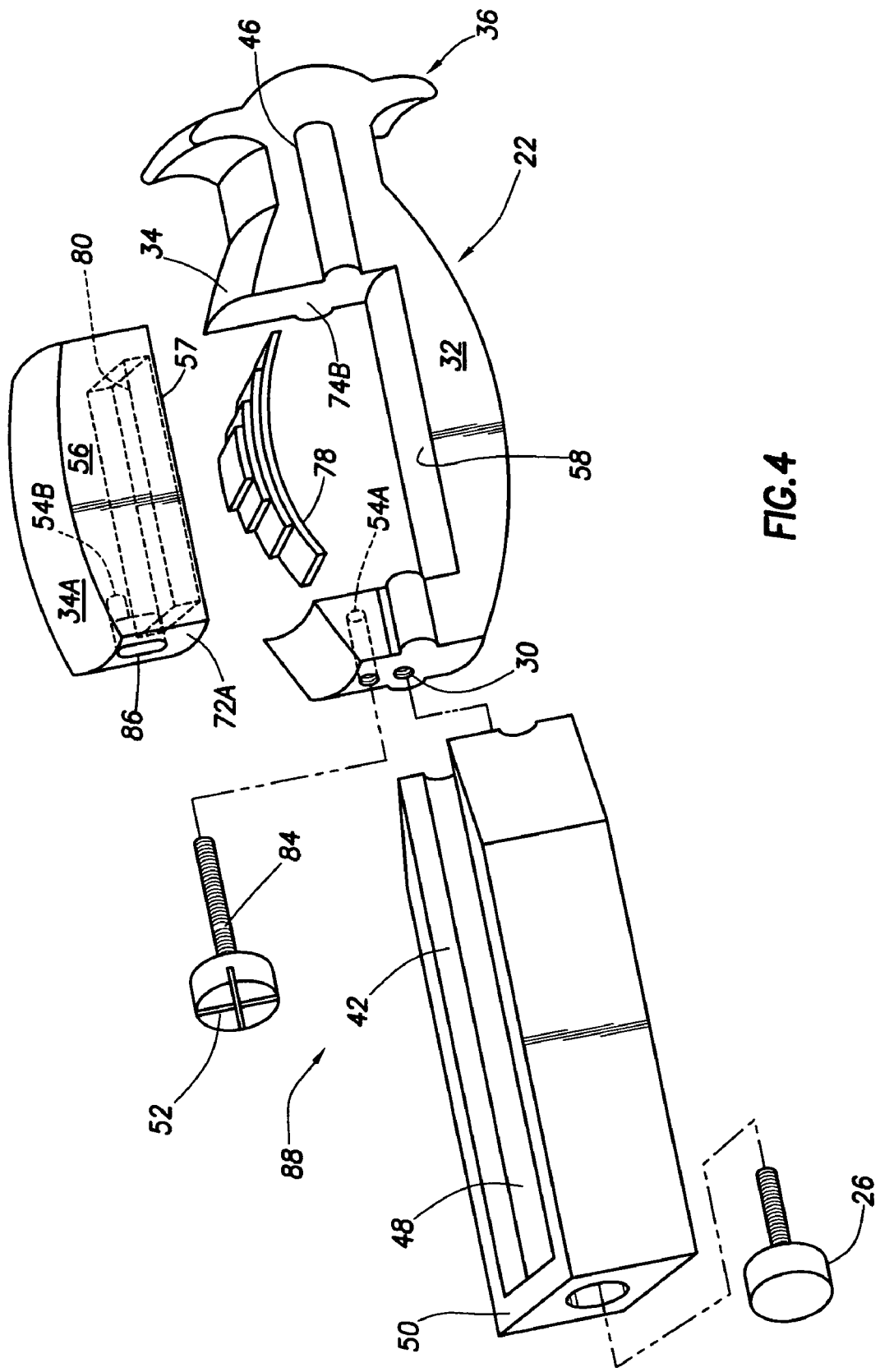
FIG. 4 is an exploded, perspective view of a fourth embodiment of a vertebral disk stabilizer constructed in accordance with the teachings of the present invention.

A third embodiment of a stabilizer constructed in accordance with the teachings of the present invention is indicated generally at reference numeral 82 in FIG. 3. Stabilizer 82 differs from stabilizer 20 (FIG. 1) in that the threaded portion of bolt 52 is provided with a weak point, indicated at reference numeral 84, and that either a portion of bore 54A extending through implant 22 or a portion of the bolt 52 proximate the head thereof is unthreaded. Bolt 52 initially resides in the bore 54 extending through the end 25 of implant 22 and into insert 56 to hold insert 56 in the first position in which the coil springs 60 are compressed and the underside 57 of insert 56 is proximate the landing 58 of implant 22 while implant 22 is inserted into the disk space and then rotated approximately 90° as described briefly above and in more detail below. Bolt 52 is then backed out of bore 54 until it extends only part way into the bore 54B in insert 56, freeing insert 56 from the first, compressed position in which the underside 57 of insert 56 is proximate the landing 58 of implant 22 so that it is biased away from landing 58 by springs 60. The bolt 52 is then broken at the point 84 and the head and broken portion of bolt 52 are removed from the bore 54A and from implant 22. Of course removing the bolt 52 from the end 25 of implant 22 allows a close fit between lock 24 and the end 25 of implant 22 when lock 24 is mounted thereto. The portion of bolt 52 that remains in the threaded portion of bore 54A, after bolt 52 was backed part way out of bore 54, extends only part way into the bore 54B in insert 56 so that insert 56 is retained in alignment with implant 22 by movement of the remaining threaded portion of bolt 52 in the channel 86 formed in the surface 72A of insert 56, the bottoming out of bolt 52 in channel 86 also acting as a stop to limit the movement of insert 56 away from landing 58. Referring to FIG. 4, a fourth embodiment of a stabilizer constructed in accordance with the teachings of the present invention, shown at reference numeral 88, is likewise provided with a bolt 52 having the same break point 84 as shown in the stabilizer 82 (FIG. 3), unthreaded proximal portion of bore 54A, and channel 86, all of which function in the same manner as described in connection with the embodiment shown in FIG. 3

Figure 5:
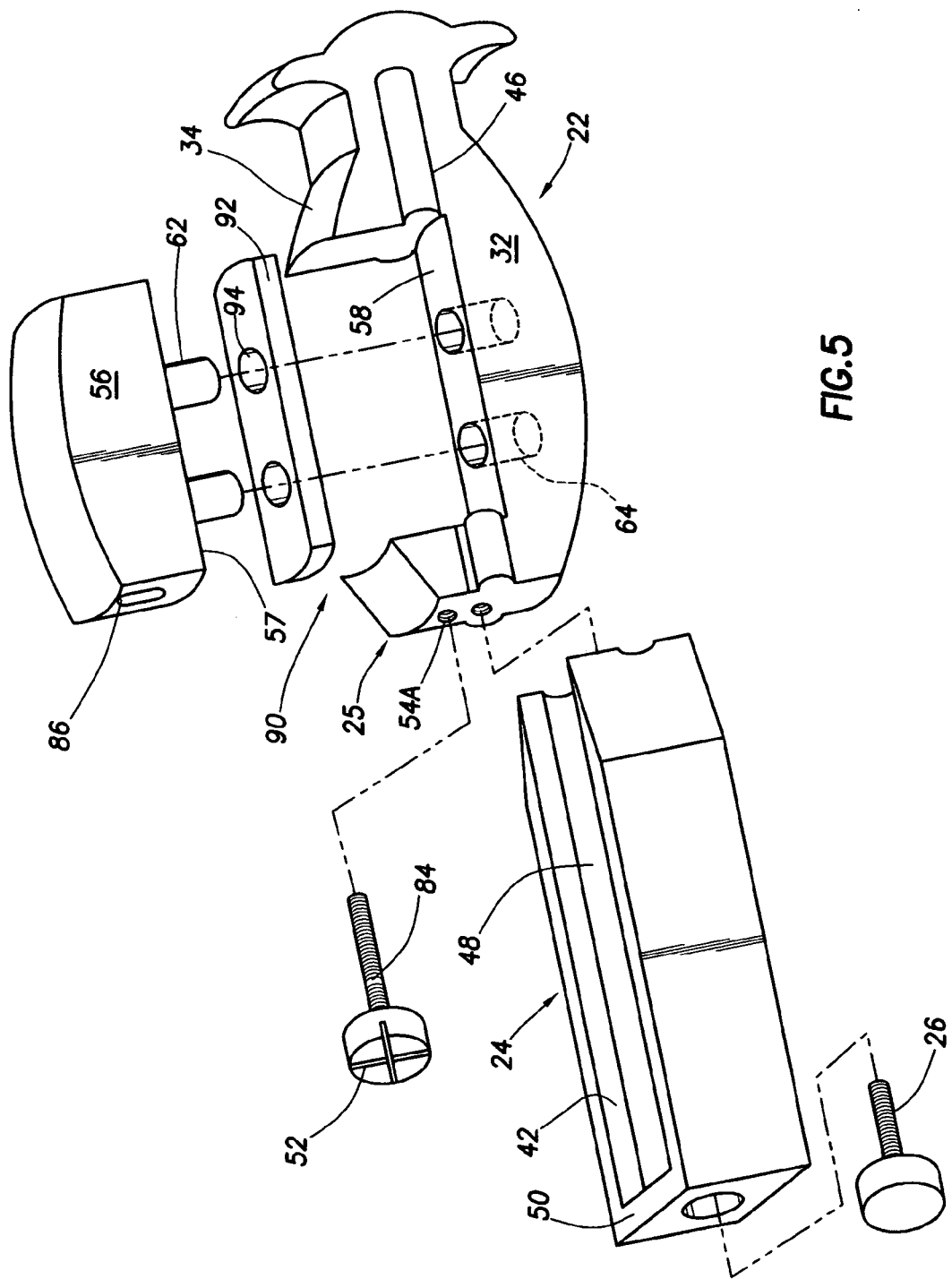
FIG. 5 is an exploded, perspective view of a fifth embodiment of a vertebral disk stabilizer constructed in accordance with the teachings of the present invention.

A fifth embodiment of a stabilizer constructed in accordance with the teachings of the present invention is designated generally by reference numeral 90 in FIG. 5. Stabilizer 90 is likewise provided with the break point 84 in bolt 52 and channel 86 in the same manner as stabilizer 82 in FIG. 3, but instead of coil springs around the pistons 62 of insert 56, stabilizer 90 is provided with a pad 92 comprised of a highly compressible, springy material that is preferably biologically inert that functions in the manner of the springs 60 shown in FIGS. 1 and 3. Such materials are known to those skilled in the art but, by way of example, certain polyurethanes and other medical grade polymers will function for the intended purpose. To insure that pad 92 is retained between the landing 58 of implant 22 and the underside 57 of insert 56, the pistons 62 of insert 56 pass through holes 94 cut through pad 92.

Referring now to FIGS. 6 and 7, a sixth embodiment of a stabilizer constructed in accordance with the teachings of the present invention is shown at reference numeral 96. Stabilizer 96 is provided with two inserts 56A and 56B on opposite sides of implant 22, each insert 56A, 56B being comprised of a compressible, springy material that is preferably biologically inert such that the entire insert 56A, 56B is biased into engagement with the adjacent vertebrae in the same manner of the springs 60 (FIGS. 1 and 3), leaf springs 78 (FIGS. 2 and 4), and pad (FIG. 5) when the band 98 that initially encircles the implant 22 (FIG. 7) is cut and then removed from the intervertebral space. Many such materials are known in the art, and by way of example, and not by way of limitation, one such material that is suitable for use in fabricating the inserts 56A, 56B is a medical grade polyurethane. As best shown in FIG. 6, the inserts 56A, 56B are shaped with flanges 100 that are received within the complementary-shaped undercuts 102 formed on both sides of implant 22 adjacent the landings 58A, 58B, and the inserts 56A, 56B are retained to and in alignment with implant 22 by the interaction between the flanges 100, undercuts 102 and the curves surfaces 72A, 72B and 74A, 74B. The three-piece implant 22 of stabilizer 96 is assembled by snapping the inserts 56A, 56B into place on either side of landings 58A, 58B, the compressible nature of the material comprising the inserts 56A, 56B providing enough resilience that the inserts 56A, 56B must be forced into place and then, once snapped into that place, retained therein.

As noted above, the key 46 and keyway 48 on implant 22 and lock 24 may be reversed from the arrangement shown in FIGS. 1-5 such that key 46 is located on lock 24 and keyway 48 is located on implant 22, and the stabilizer 96 shown in FIGS. 6 and 7 illustrates such an arrangement. The funnel-shaped portion 47 of the keyway 48 behind the mouth 45 at the end 25 of implant 22, which gradually decreases in width, acts to increase the ease with which lock 24 is mounted to implant 22 by insertion of the keys 46 on lock 24 into the respective keyways 48 on implant 22 and helps to seat lock 24 thereon and align the bore 28 in lock 24 with the bore 30 in implant 22.

Figure 8:
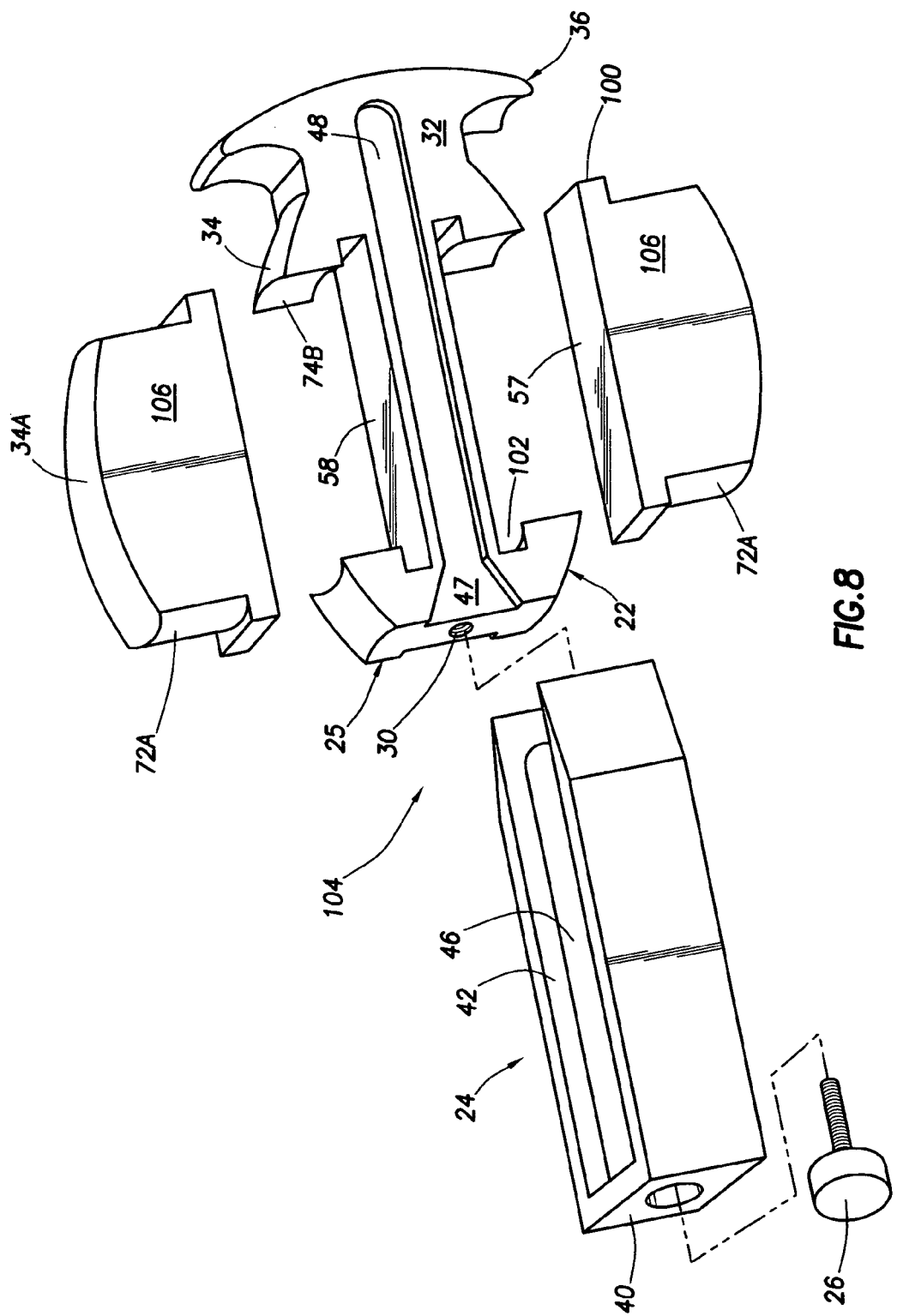
FIG. 8 is an exploded, perspective view of seventh embodiment of a vertebral disk stabilizer constructed in accordance with the teachings of the present invention.

Referring now to FIG. 8, there is shown another alternative embodiment of a stabilizer 104 constructed in accordance with the teachings of the present invention. Implant 104 differs from the implants 22 of stabilizer 20 (FIG. 1), stabilizer 76 (FIG. 2), stablizer 82 (FIG. 3), stabilizer 88 (FIG. 4), stabilizer 90 (FIG. 5), or stabilizer 96 (FIGS. 6-7) in that the inserts 106 comprising a portion of implant 104 are sized so that the surface 34A of insert 106 extends out of, or are not flush with, the surface 34 of implant 104. As with the inserts 56 of stabilizer 96 (FIGS. 6-7), the inserts 106 of implant 104 are comprised of a material that is highly compressible and springy, or spongy, and that is preferably biologically inert, and is initially compressed by a band in the same manner as shown in FIG. 7. However, rather than being biased away from implant 104, the entire insert 106 functions as a cushion between vertebrae in the same manner as described in connection with the embodiments shown in FIGS. 1-7.

The use of the stabilizer of the present invention in, for instance, a method of lumbar intervertebral disk stabilization will now be described. Surgery is performed as in a simple diskectomy and the intervertebral disk 20 is exposed through a small laminotomy. The herniated portion of the disk is removed and any nerve root compression is corrected. The posterior longitudinal ligament (not shown) and disk cartilage are removed until the surfaces of the bodies of the adjacent vertebrae are exposed above and below the disk space, but the portions of the disk on either side of the defect are retained.

Using spreaders such as those disclosed in International Application No. PCT/US95/00347, which reference is hereby incorporated into this specification in its entirety by this specific reference thereto, the adjacent vertebrae are distracted to open the disk space, and once the desired "spread" is achieved, an appropriately-sized implant 22 is then inserted into the disk space using the above-described applicator with the implant 22 oriented so that the top and bottom thereof, i.e., the first and second sides 32, engage the bodies of the adjacent vertebrae. As noted above, it is not necessary to remove the remainder of the intervertebral disk or to pack the disk space with cancellous bone chips as with prior known surgical methods. The positioning of the lock 24 at the opening to the disk space as described below virtually seals off the opening to the disk space, making the likelihood of recurring herniation of the disk negligible. Further, the posterior longitudinal ligament is left intact to the opposite side and to the center of the disk space.

The present invention also contemplates the use of a medical grade adhesive in sealing the opening to the disk space. Another modification of the method described herein is the use of various hydrogels, either with or without an adhesive, in the intervertebral space. One type of hydrogel that is suitable for the intended purpose is a group of polymers referred to as protein polymers. These polymers are described, for instance, in U.S. Pat. Nos. 5,514,581 and 6,184,348 and in D. C. Martin, et al., "Processing and characterization of protein polymers," in Protein-Based Materials, K. McGrath and D. Kaplan, Eds. (1996). Various biologically-inert polyvinylpyrolidine (PVP) polymers are also known that function for the intended purpose, as are such polymeric materials as the modified collagen matrix disclosed in U.S. Pat. Nos. 5,147,514, 5,332,475, 5,854,397 and European Patent No. 0411925. Other suitable materials are known to those skilled in the art and are referred to collectively herein as hydrogels because of their highly viscous properties under physiological conditions. These hydrogels are injected or otherwise introduced into the intervertebral disk space before or after the implant 22 is inserted to fill the space around the implant and the highly viscous "glob" fills the voids in the disk space and functions to help retain the remaining portion of the intervertebral disk intact and further reduce the likelihood of any recurrent herniation of the disk from the opening into the disk space. Depending upon the condition of the remaining portion of the disk, if necessary, the disk space may also be injected or otherwise provided with the above-described medical grade adhesive for the purpose of helping bind the hydrogel to the disk material and/or helping to maintain the integrity of the remaining disk material.

Using the applicator, the implant 22 is positioned in the disk space at a position in which the expanded, middle portion and the smaller width ends 25 and 36 of the third and fourth sides 34 of implant 22 contact the respective lower and upper surfaces of the bodies of the adjacent vertebrae when rotated by approximately 90°. The respective lower and upper surfaces of the vertebral bodies are slightly concave such that the larger width middle portion of implant 22 allows the implant 22 to engage substantially more of the surfaces of the vertebral bodies of the adjacent verterbrae than conventional prosthetic devices, thereby providing increased stability to the implant once further rotation of implant 22 in the disk space is prevented as described below.

Once positioned in the disk space so as to provide maximum stabilization, the applicator is detached from implant 22 by backing the applicator out of the incision in the patient. Lock 24 is then inserted through that same incision and, using the key 46 and keyway 48, the bore 28 in lock 24 and bore 30 in implant 22 are aligned and the bolt 26 is inserted and tightened to secure lock 24 to the implant 22. Securing the lock 24 to implant 22 in this manner resists relative rotation between lock 24 and implant 22 and the bearing surfaces 50 of lock 24 bear against the bodies of the adjacent vertebrae to resist rotation of the lock 24 relative to the adjacent vertebrae against which the bearing surfaces 50 bear. Those skilled in the art who have the benefit of this disclosure will recognize that the bearing surfaces 50 bear against the cortical end plate of the respective vertebral bodies, which is comprised of non-cancellous bone, and provides a hard, relatively smooth surface against which the bearing surfaces 50 bear. When mounted to the end 25 of implant 22 with the bearing surfaces 50 bearing against one or more of the adjacent vertebrae, the bearing surfaces 50 of lock 24 are oriented at an angle of approximately 90° to the height of implant 22. The end 40 of lock 24 is preferably supplied in a plurality of different sizes and shapes other than the square shaped end 40 shown in the figures so as to allow the surgeon to select an appropriately-sized and shaped lock that provides a close fit with the space between vertebral bodies.

If required at a later date, removal of implant 22 from the intervertebral disk space is accomplished with relative ease compared to conventional implants. The bolt 26 is screwed back out of implant 22 and lock 24 is pulled out of the disk space. An applicator of the type described in the above-incorporated U.S. Pat. No. 5,658,336 is inserted into the disk space and screwed into the bore 30 in implant 22 and used to rotate implant 22 by approximately an additional 90°, causing the first and second sides, having minimal height, to contact the bodies 12 and 14 of adjacent vertebrae 16 and 18 so as to allow posteriorly-directed movement of the implant 22 out of the disk space.

Although described in terms of the embodiments shown in the figures, these embodiments are shown to exemplify the present invention and not to limit the scope of the invention, it being recognized by those skilled in the art that certain changes can be made to the specific structure of the embodiments shown and described without departing from the spirit of the present invention. In the case of one such change, the first and second sides of the implant are substantially flat but not parallel along their longitudinal axes so that the implant is wedge-shaped. The wedge shape of the implant facilitates insertion of the implant into the disk space, the rounded end of the implant reducing the likelihood of injury to the nerves of the spinal cord during insertion into the disk space. Likewise, the width at one end of the implant can be less than the width at the end, both widths, however, being less than the width in the middle, expanded portion of the implant. Further, the connection by which lock 24 is mounted to implant 22 is capable of being constructed in a manner different than that shown in the figures herein. Another such modification relates to manner in which the insert 56 is retained in the first and/or compressed position proximate landing 58, it being recognized by those skilled in the art that instead of using the bolt 52 for that purpose, the key 46 and keyway 48 may be used to restrain movement of insert 56 away from landing 58. Another modification relates to the above-described medical grade adhesive and protein polymers. As noted above, an adhesive may be utilized to seal the opening to the disk space and/or to facilitate bonding of the protein polymer or other type of hydrogel to the remaining disk material. To facilitate that function, the bore 28 in lock 24 is provided with a reservoir of adhesive that, when punctured by insertion of the bolt 26 therein, causes the adhesive to exude out of bore 28 and into the opening to the disk space as the bolt 26 squeezes the contents from the reservoir as it is tightened against the lock 24. Similarly, implant 22 is provided with a reservoir of protein polymers, for instance, at the end 36 that is punctured by the point of the key 46 as the key slides into a keyway such as the keyway 48 on both sides of the implant 22 of stabilizer 96 shown in FIGS. 6 and 7. All such modifications, and other modifications that do not depart from the spirit of the present invention, are intended to fall within the scope of the following claims.

What is claimed is:

1. A method of cushioning between an elongate implant positioned in a space from which a portion of an intervertebral disk has been removed and the vertebra adjacent the disk space, the implant having a substantially rectangular cross-sectional shape and a height greater than the width of the implant, comprising the steps of:
   inserting the implant into the intervertebral disk space with the sides of the implant defining the height of the implant in contact with the adjacent vertebra, the implant having an insert mounted thereto on a spring and movable relative to the implant, the insert being restrained against movement relative to the implant;
   rotating the implant along the longitudinal axis thereof so that the sides of the implant defining the width of the implant contact the adjacent vertebra; and
   releasing the insert so as to bias the insert away from the implant toward the adjacent vertebra with the spring.

2. A method of stabilizing two vertebrae comprising the steps of:
   removing a portion of the intervertebral disk of a patient;
   inserting an elongate implant having an insert movably mounted thereto into the space from which a portion of the intervertebral disk has been removed;
   rotating the implant along the longitudinal axis of the implant after the implant in inserted into the disk space;
   restraining the movable insert against movement relative to the implant until the implant is inserted into the disk space, after which the movable insert is released so as to bias the movable insert into engagement with a vertebra adjacent the intervertebral disk space; and
   resisting rotation of the implant along the longitudinal axis of the implant.

3. The method of claim 2 additionally comprising filling any space between the implant and the two vertebrae with a hydrogel.

4. The method of claim 3 wherein said hydrogel is selected from the group consisting of protein polymers, polyvinylpyrollidone polymers, and modified collagen matrix.

5. The method of claim 3 additionally comprising contacting the remaining portion of the intervertebral disk, or the hydrogel, or both the remaining portion of the intervertebral disk and the hydrogel with a medical grade adhesive.

6. The method of claim 2 additionally comprising sealing the intervertebral disk space with a medical grade polymer.

7. The method of claim 2 wherein the insert comprises a metal or other relatively incompressible material and is biased away from the implant into engagement with the adjacent vertebra by a spring.

8. The method of claim 7 additionally comprising restraining the insert against movement relative to the implant until after the implant is inserted into the intervertebral disk space from which a portion of the intervertebral disk has been removed.

9. The method of claim 2 wherein the implant comprises a metal or other relatively incompressible material and the insert comprises a springy, compressible material that provides a cushioning effect when engaged by the adjacent vertebrae.

10. The method of claim 9 additionally comprising compressing the insert before inserting the implant and insert into the intervertebral disk space from which a portion of the intervertebral disk has been removed and then releasing the insert from the initial, compressed state into engagement with the adjacent vertebra.

11. The method of claim 1 additionally comprising restraining the insert against movement relative to the implant until after the implant is inserted into the intervertebral disk space from which a portion of the intervertebral disk has been removed.

12. The method of claim 1 wherein the implant comprises a metal or other relatively incompressible material and the insert comprises a compressible material that provides a cushioning effect when engaged by the adjacent vertebrae.

13. The method of claim 12 additionally comprising compressing the insert before inserting the implant into the intervertebral disk space from which a portion of the intervertebral disk has been removed and then releasing the insert from the initial, compressed state into engagement with the adjacent vertebra.

14. The method of claim 1 additionally comprising maintaining alignment of the implant and the insert while biasing the insert away from the implant.

15. The method of claim 1 additionally comprising resisting rotation of the implant in the intervertebral disk space.

16. The method of claim 1 additionally comprising limiting the movement of the insert away from the implant.

17. The method of claim 1 additionally comprising resisting movement of the implant out of the intervertebral disk space.

18. The method of claim 2 additionally comprising resisting movement of the implant out of the intervertebral disk space.

* * * * *